United States Patent
Salmeia et al.

(10) Patent No.: US 10,968,204 B2
(45) Date of Patent: Apr. 6, 2021

(54) FLAME RETARDANTS

(71) Applicants: EMPA Swiss Federal Laboratories for Materials Science and Technology, Duebendorf (CH); Bruag Fire Protection AG, Guettingen (CH)

(72) Inventors: Khalifah Salmeia, St. Gallen (CH); Sabyasachi Gaan, Gossau (CH); Markus Brühwiler, Uttwil (CH)

(73) Assignees: Bruag Fire Protection AG, Guettingen (CH); EMPA Swiss Federal Laboratories for Materials Science and Technology, Duebendorf (CH)

( * ) Notice: Subject to any disclaimer, the term of this patent is extended or adjusted under 35 U.S.C. 154(b) by 0 days.

(21) Appl. No.: 16/339,787

(22) PCT Filed: Oct. 9, 2017

(86) PCT No.: PCT/EP2017/075677
§ 371 (c)(1),
(2) Date: Apr. 5, 2019

(87) PCT Pub. No.: WO2018/069249
PCT Pub. Date: Apr. 19, 2018

(65) Prior Publication Data
US 2020/0039962 A1 Feb. 6, 2020

(30) Foreign Application Priority Data
Oct. 12, 2016 (DE) .................. 20 2016 006 301 U

(51) Int. Cl.
*C07D 403/12* (2006.01)

(52) U.S. Cl.
CPC ................. *C07D 403/12* (2013.01)

(58) Field of Classification Search
CPC .................................................. C07D 403/12
See application file for complete search history.

(56) References Cited

U.S. PATENT DOCUMENTS

| | | | |
|---|---|---|---|
| 4,038,197 A | 7/1977 | Caspari | |
| 7,654,877 B2 | 1/2010 | Gmeiner et al. | |
| 8,754,154 B2 | 6/2014 | Dave et al. | |

FOREIGN PATENT DOCUMENTS

| | | |
|---|---|---|
| EP | 0551153 A1 | 7/1993 |
| EP | 0551154 A1 | 7/1993 |
| EP | 2371890 A1 | 10/2011 |
| EP | 2183314 B1 | 12/2011 |
| WO | 2006034784 A1 | 4/2006 |
| WO | WO 2006/034784 * 4/2006 ............ C07F 9/6561 |

OTHER PUBLICATIONS

Kreher, T., et al, Dynamische NMR-Untersuchungen von Phosphorylierten Diamin-gekoppelten Bis-1,25-triazinen, Phosphorus, Sulfur, and Silicon and the Related Elements, 141:1, 135-146 (2017) (Year: 2017).*

Kreher, et al., "Dynamische NMR-Untersuchungen von phosphorylierten Diamin-gekoppelten Bis-1, 3, 5-triazinen," Phosphorus, Sulfur and Silicon and the Related Elements (1998), vol. 141, pp. 135-146.

International Search Report and Written Opinion for International Application No. PCT/EP2017/075677 dated Jan. 16, 2018 (11 pages).

* cited by examiner

*Primary Examiner* — Erich A Leeser
(74) *Attorney, Agent, or Firm* — Fitch, Even, Tabin & Flannery LLP

(57) ABSTRACT

The invention relates to flame retardants comprising atriazine compound according to Formula 1: (1) with R=phosphite substituted with alkyl, functionalized alkyl, aryl, functionalized aryl, except halogen-substituted alkyl or aryl; R'=alkylene, arylene, alkoxy or aryloxy, all unsubstituted or functionalized, except halogen-substituted; $X_1$ and $X_2$=hetero atoms and $X_1=X_2$ or $X_1$ not=$X_2$ and to specific triazine compounds as such.

(1)

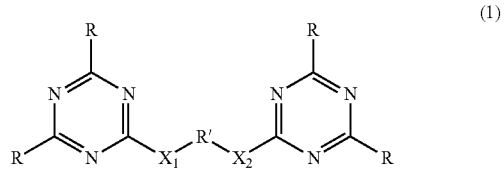

26 Claims, No Drawings

FLAME RETARDANTS

The invention relates to flame retardants which contain triazine compounds having alkyl functionalized alkyl, aromatic or functionalized aromatic, substituted phosphite groups, as well as such compounds and their use in flame retardants.

Flame retardants are widely used for fire protection. They are intended to reduce the flammability of combustible materials, such as wood or plastic, and are added to corresponding protective coatings for the material or incorporated into the material to be protected.

Flame retardants are the subject of various industrial standards. For wood, e. g. DIN 4102 is specifically relevant in Germany. For plastics, e. g. DIN EN ISO 1043-4 applies. Within the scope of this invention, flame retardants which conform to DIN 4102 B1 are especially relevant.

Triazine compounds are generally already known as effective components of flame retardants. One example is tris (tribromophenoxy)-s-triazine, which has been used, for example, in polyethylene films. However, halogen-containing flame retardants are subject to increasing criticism because under the influence of heat, they can liberate halogen compounds which are highly harmful to health.

There is therefore a need for effective flame retardants which do not contain relevant amounts of halogens.

Halogen-free phosphorus-containing triazine compounds have been described as flame retardants, for example, in EP 2,183,314 and EP 2,371,890. These compounds are melamine derivatives which are converted to polycondensation molecules.

Compounds comprising two bis-(2,4-dialkylphosphite) triazine groups linked by a bridge group derived from ethylenediamine according to Formula 2 are known from EP 0 551 153 A1 and EP 0551 154 A1, where they are used as intermediates in the production of 2,4-diamino-1,3,5-triazinyl-6-phosphoric acid derivatives.

The derivatives are used in self-extinguishing polymeric compositions.

FORMULA 2

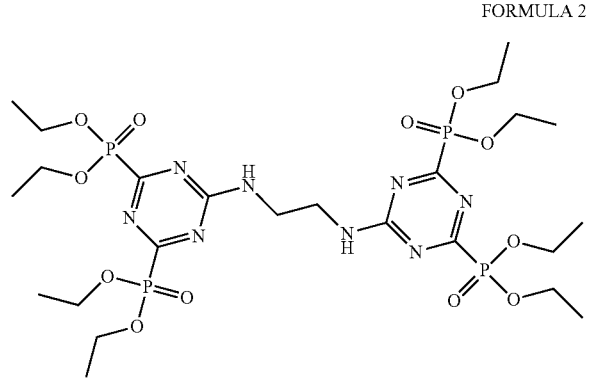 [SMILES: CCOP(=O)(OCC)c1nc(NCCNc2nc(P(=O)(OCC)OCC)nc(P(=O)(OCC)OCC)n2)nc(P(=O)(OCC)OCC)n1]

Compounds according to Formula 2 are also known from T. Kreher et al., Phosphorus, Sulfur and Silicon and the Related Elements (1998), 141, 135-146, where their properties were investigated by dynamic NMR. These studies bear no relationship to flame retardant applications.

Against this background, it is an object of the invention to provide novel substances which are suitable as flame retardants and flame retardants comprising these, which can be produced simply and inexpensively, in particular from commercially available starting materials.

A further object of the invention is to provide such flame retardants which can be used simply and in various ways in paints, coatings and the like, as well as ingredients in solid materials.

These and other objects, which will become apparent from the following description of preferred embodiments, are attained by the feature combinations of the appended independent claims.

Preferred embodiments of the invention are defined in the dependent claims.

The compounds which can be used as actives in flame retardants comprise chemical entities which are per se novel. Such compounds are defined in appended claim 1.

More specifically, these compounds correspond to Formula 1 with the following provisos:

R=phosphite substituted with alkyl, functionalized alkyl, aryl or functionalized aryl. Halogen-substituted alkyl and aryl are excluded.

R'=alkylene, arylene, alkoxy or aryloxy, all unsubstituted or substituted, except halogen-substituted;

$X_1$ and $X_2$ are hetero atoms and can be same or different.

Where $X_1$ and $X_2$ are NH, and R is ethyl,

R' is not phenylene; 2-methyl-1,3-phenylene;

2,4,6-trimethyl-phenylene;

1,3-xylylene; diphenylmethane-4,4'-diyl;

1,2-ethylene; 1,3-propylene; 1,6-hexylene;

1,8-(3,6-dioxa octylene) or pyrid-2,6-diyl;

Where $X_1$ and $X_2$ are NH and R is methyl,

R is not 1,3-phenylene or dimethyl-1,3-propylene.

Where $X_1$ and $X_2$ are NH and R is iso-propyl, R' is not 1,3-phenylene or 1,12-dodecylene.

Especially preferred embodiments of these new compounds are defined in the subclaims of claim 1

FORMULA 1

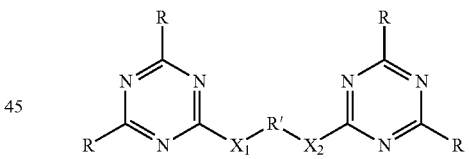

According to the invention, compounds of the general Formula 1 which contain two bis (2,4-dialkylphosphite) triazine moieties bridged by a $X_1$—R'—$X_2$ group (the "bridge group") as defined in claim 6 can be used in flame retardants or as flame retardants, as defined in claim 6.

In these flame retardant actives according to Formula 1,

R is phosphite substituted with alkyl, functionalized alkyl, aryl or functionalized aryl, except halogen-substituted alkyl or aryl.

R' is alkylene, arylene, alkoxy or aryloxy, all unsubstituted or functionalized, except halogen-substituted;

$X_1$ and $X_2$ are hetero atoms.

$X_1$ and $X_2$ can be the same or different.

The bridge group $X_1$—R'—$X_2$ appears to be of specific relevance for the usefulness of these compounds as flame retardants. It also has a marked influence on their physical and flame retardant properties, including their solubility.

In preferred embodiments of the invention, the substituents shown in Formula 1 comprise the following moieties:

R:
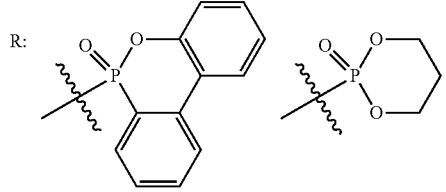

(Z = methyl, ethyl, propyl, butyl, tert-butyl, isobutyl, isopropyl, phenyl)

R':
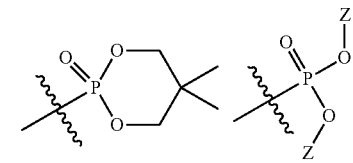

1p; 2p
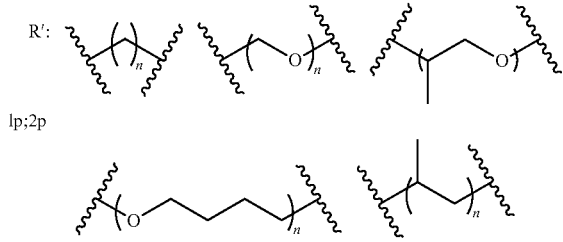

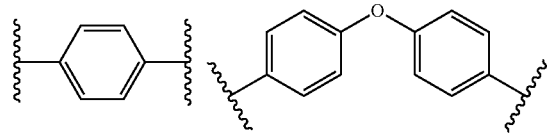

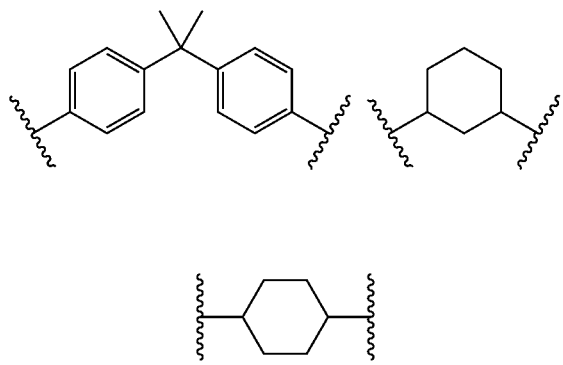

$X_1 = X_2 = O, NH$
$X_1 \neq X_2 = O, NH$

More specifically, R is preferably dialkylphosphite, especially diethyl- or dimethylphosphite. R' is preferably alkyl with n=1 to 10, more preferred 1 to 6 and most preferred 1 to 3, especially n=2. $X_1$ and $X_2$ are preferably both NH.

Preferred embodiments of the invention comprise flame retardants comprising compounds according to Formulae 2 to 5, as follow:

FORMULA 2
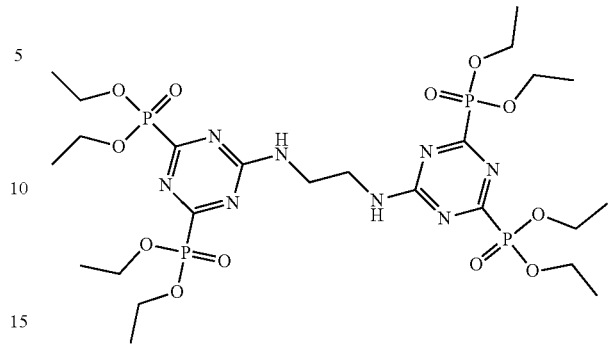

FORMULA 3
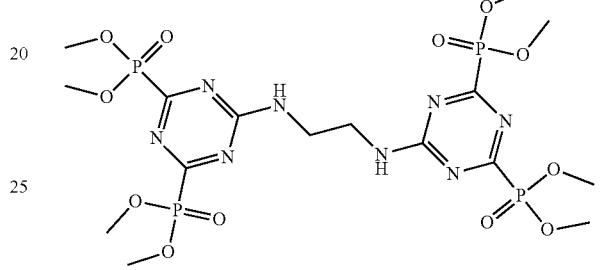

FORMULA 4
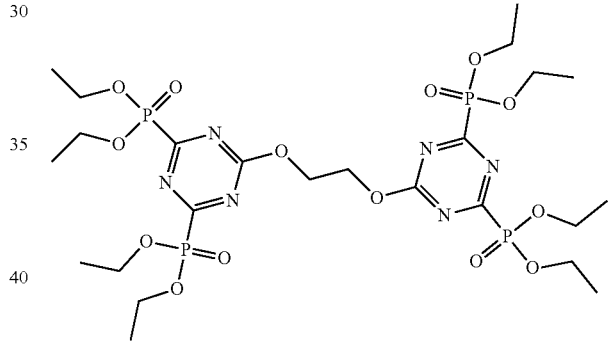

FORMULA 5
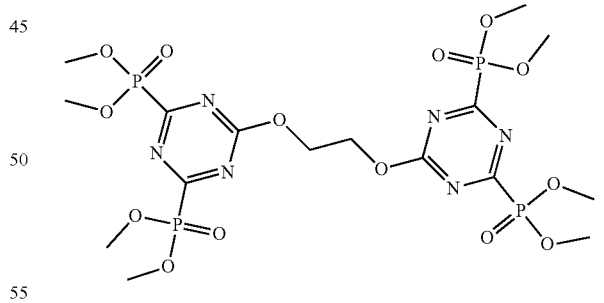

As already mentioned above, the two hetero functions of the bridge group do not have to be the same. E.g. one can be NH while the other is O. Other hetero functions can be used instead of NH or O, e.g. Si or S. It is however strongly preferred that $X_1$ and $X_2$ both comprise heteroatoms, i. e. the atoms connecting the bridge group to the triazine moieties are not C.

It can further be seen that the bridge group is, in preferred embodiments, based on short chain alkylene. In Formulae 2 to 5, this is ethylene. Generally, the alkylene chain can be longer but should not be too long, or it will affect the overall character of the molecule too much. Alkylene with up to 10, preferably up to 6 and especially between 1 and 3 is preferred.

The synthesis of the particularly preferred compound shown in Formula 2 is carried out by reacting tris (2,4,6-diethylphosphite)-s-triazine with ethylenediamine. According to U.S. Pat. No. 4,038,197 (the disclosure of which is hereby incorporated by reference), tris (2,4,6-diethylphosphite)-s-triazine can be obtained by reacting cyanuric chloride with triethylphosphite. Ethylenediamine is a commercially available basic chemical.

In the reaction according to the invention, both amino groups of the ethylenediamine (EDA) react with a diethylphosphite group of one molecule of the substituted triazine (HEPT) each, to form the compound shown in Formula 2 according to the following reaction scheme:

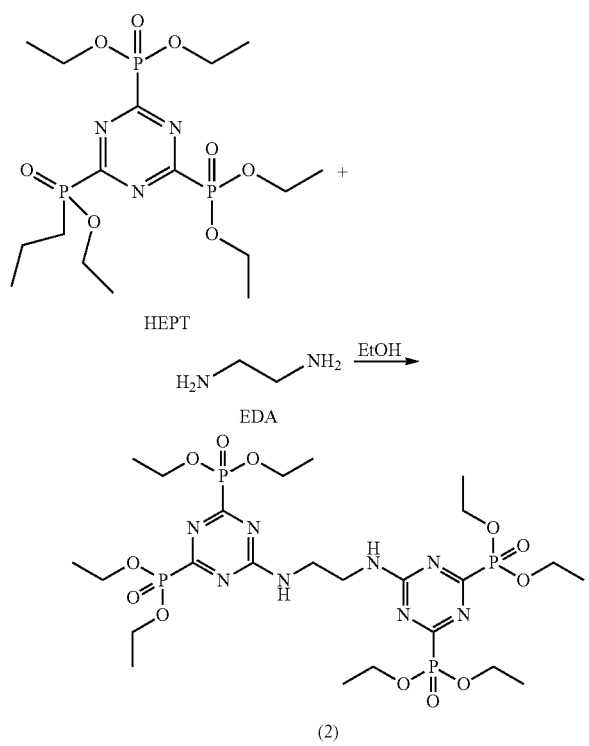

(2)

The other compounds of the invention can be synthesized by similar methods.

In the synthesis of the other compounds, the bridge group can be formed from corresponding alkylene diamines, if $X_1$ and $X_2$ are NH. If $X_1$ and $X_2$ are O, the bridge group can e.g. be formed from ethylene glycol.

If only one of $X_1$ or $X_2$ is NH and the other is O, suitable bridge group reactants e.g. comprise ethanolamine.

The flame retardants according to the invention contain the abovementioned triazine compounds either in a mixture with other constituents, for example other flame retardants, solvents, solid or liquid carriers, stabilizers and the like, or consist of one or more of the triazine compounds in pure form ("neat"). A pure form in the sense of the invention consists predominantly (from more than 90%, preferably more than 98%, within usual analytical determination accuracy) of the triazine compounds described above. (All percentages in this specification are weight percent based on total weight, unless otherwise defined.)

In preferred embodiments, a flame retardant according to the invention contains further flame retardants which interact with the described triazines. Examples are DMMP (dimethyl methylphosphonate) and phosphoric acid esters such as PEPA.

The flame retardants according to the invention can be incorporated into paints, coatings, coatings and the like for flammable materials.

They can preferably also be incorporated into the solid material. For example, in the production of wood-based materials, such as chipboards and the like, the flame retardant according to the invention can be introduced into the binder resin by which the chip material is glued. In the case of plastic parts, the flame retardant according to the invention can be admixed with the plastic or synthetic resin composition before its shaping and curing.

The flame retardants according to the invention are fire-retardant even at low concentrations (10% by weight) and are flame-retardant in higher concentrations. They have high flame protection efficiency and are self-extinguishing. They reduce flame emanation and are suitable for products meeting the requirements of DIN 4102 B1.

Conventional concentrations of the flame retardant in paints are between 10% and 30%, based on the total weight of the coating material. In coatings, for example for wood-based boards, the concentration is usually between 10% and 20%.

As a component of solid material, typical concentrations of the flame retardant are between 1% and 5%, but can be higher, up to 10% or even above 10%.

The flame retardants of the invention can be used in water-based paint systems and solutions. They are compatible with UV varnish. They are not dangerous goods within the meaning of legal requirements and, due to their halogen-free nature, are compatible with the environment.

When used in lacquer systems, for example, the flame retardant is mixed into the starting lacquer so that the final product consists of 10% flame retardant and 90% varnish. The flame retardant preferably contains only the flame-retardant substances, i.e., no relevant proportions of solvents and the like. The end product can be processed in the same way as the initial lacquer. Since the flame retardant is colourless, the properties of the lacquer are not significantly affected.

In flameboard and MDF boards, flame retardants according to the invention can be introduced by vacuum infiltration. Alternatively, the flame retardants can be added to the chips during the production of the board and processed together therewith.

EMBODIMENT EXAMPLES

A. In a 5 liter four-necked flask equipped with nitrogen feed, reflux condenser, mechanical stirrer, blower counter and thermometer, 481.1 g of tris (2,4,6-diethylphosphite)-s-triazine, in abs. Ethanol, 28.13 g of ethylenediamine are added dropwise at RT. After the addition was complete, the mixture was stirred at RT for 3 h. Subsequently, the batch was concentrated under vacuum and the solid residue was filtered off. Further solid was recovered by cooling overnight and re-filtering. The combined solid fractions were washed with heptane and dried under vacuum at 60° C.

The product was the compound shown in Formula 2.
Analysis:
Cumulative formula $C_{24}H_{46}N_8O_{12}P_4$
Molecular weight 762.57105
Elemental Analysis C, 37.80; H, 6.08; N, 14.69; O, 25.18; P, 16.25

The product obtained is a free-flowing white powder, which can be admixed in usual commercially available coatings and bulk materials without any problems.

B. HEPT (13.9 Kg) was dissolved in absolute ethanol (50 L). Ethylene diamine (845.14 g) was then added dropwise by dropping funnel at ambient temperature. After complete addition, the reaction mixture was stirred at ambient temperature for 4 h, affording a yellow solution. The volatiles were then completely removed under vacuum, resulting in yellow viscous oil. Toluene (30 L) was then added with vigorous stirring. While stirring, the product formed as white powder which was collected by filtration, washed with Toluene (20 L) and then dried in vacuum at 60° C. Yield: 8.19 Kg (75.6%).

The product corresponds to Formula 2.

The invention claimed is:

1. A water- or lacquer-based coating for a flammable material comprising 10-30% of a compound according to Formula 1:

FORMULA 1

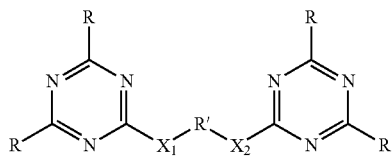

with R=phosphite substituted with alkyl, functionalized alkyl, aryl, functionalized aryl, except halogen-substituted alkyl or aryl;
R'=alkylene, arylene, alkoxy or aryloxy, all unsubstituted or functionalized, except halogen-substituted;
$X_1$ and $X_2$=hetero atoms and $X_1$ and $X_2$ are the same or different.

2. The coating as claimed in claim 1, wherein R comprises one or more of the following:

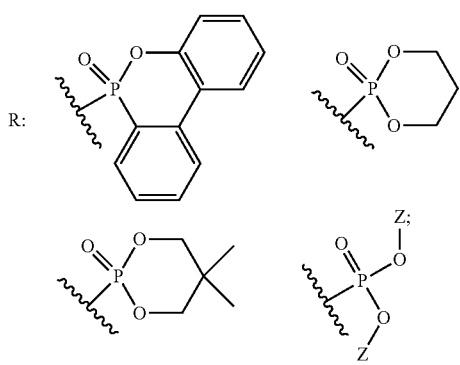

wherein Z comprises methyl, ethyl, propyl, butyl, tert-butyl, isobutyl, isopropyl, or phenyl;

wherein R' comprises one or more of the following:

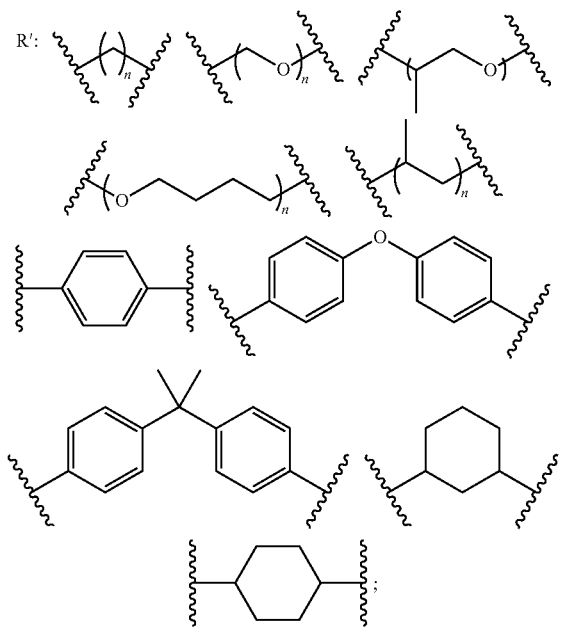

wherein $X_1$ and $X_2$ are the same or different and each comprises O or NH.

3. The coating of claim 1 comprising a compound according to Formula 2:

(2)

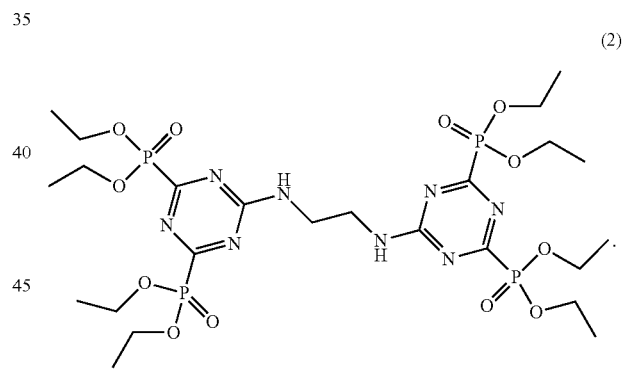

4. The coating of claim 1, comprising a compound according to Formula 3:

(3)

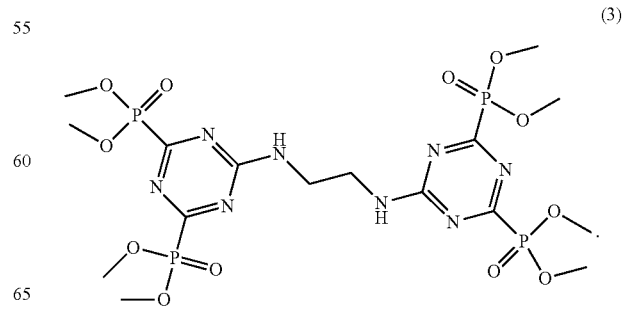

5. The coating of claim 1, comprising a compound according to Formula 4:

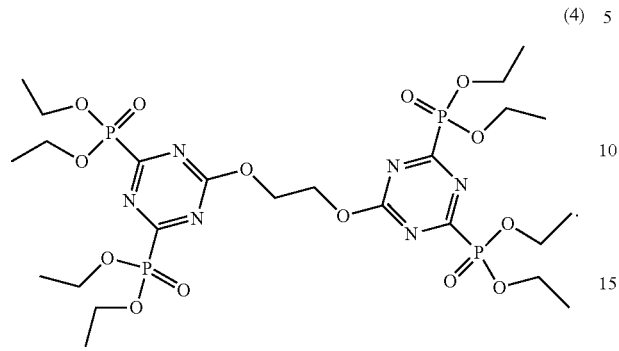
(4)

6. The coating of claim 1, comprising a compound according to Formula 5:

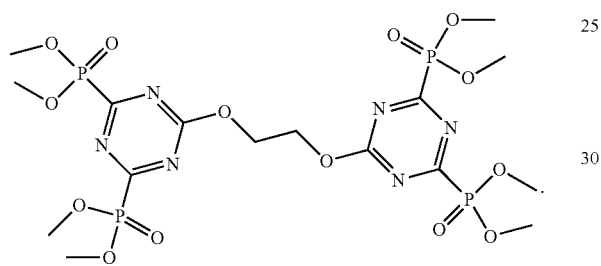
(5)

7. A solid wood or plastic material comprising a compound according to Formula 1:

FORMULA 1

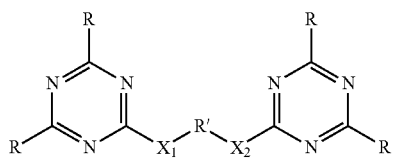

with R=phosphite substituted with alkyl, functionalized alkyl, aryl, functionalized aryl, except halogen-substituted alkyl or aryl;
R'=alkylene, arylene, alkoxy or aryloxy, all unsubstituted or functionalized, except halogen-substituted;
$X_1$ and $X_2$=hetero atoms and $X_1$ and $X_2$ are the same or different.

8. The solid material of claim 7, wherein R comprises one or more of the following:

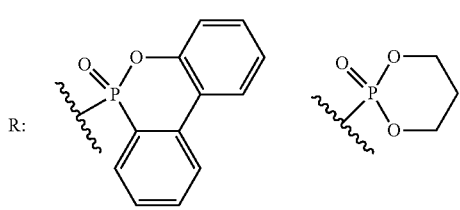

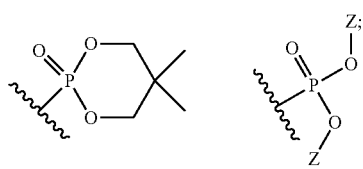

wherein Z comprises methyl, ethyl, propyl, butyl, tert-butyl, isobutyl, isopropyl, or phenyl;

wherein R' comprises one or more of the following:

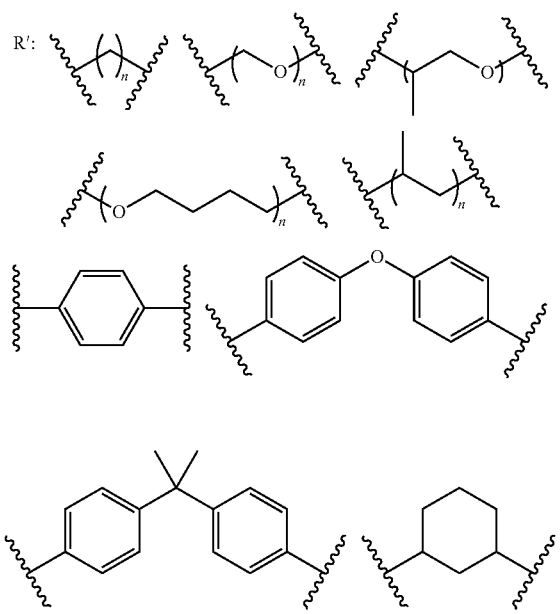

wherein $X_1$ and $X_2$ are the same or different and each comprises O or NH.

9. The solid material of claim 7, comprising a compound according to Formula 2:

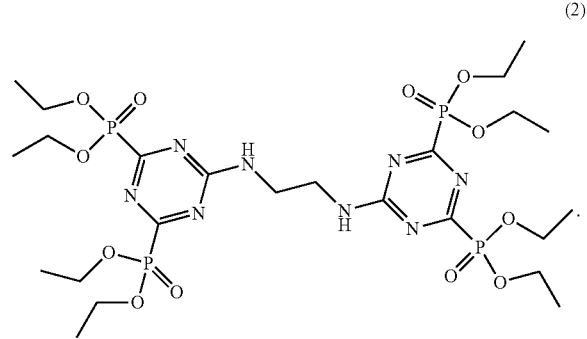 [SMILES: CCOP(=O)(OCC)c1nc(NCCNc2nc(P(=O)(OCC)OCC)nc(P(=O)(OCC)OCC)n2)nc(P(=O)(OCC)OCC)n1]
(2)

10. The solid material of claim 7, comprising a compound according to Formula 3:

(3)

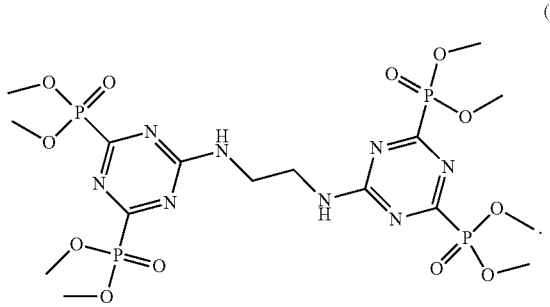

11. The solid material of claim 7, comprising a compound according to Formula 4:

(4)

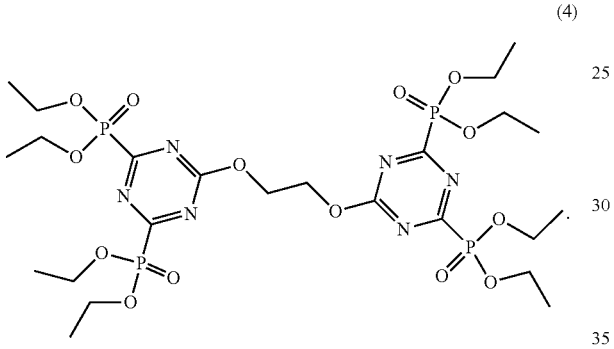

12. The solid material of claim 7, comprising a compound according to Formula 5:

(5)

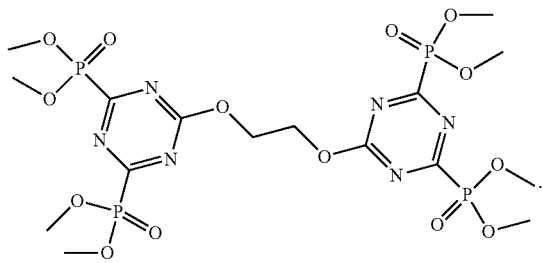

13. The solid material of claim 7, comprising the compound of Formula 1 at a concentration above 1 wt. % based on total wt. of the product.

14. The solid material of claim 7, comprising the compound of Formula 1 at a concentration above 2 wt. % based on total wt. of the product.

15. The solid material of claim 7, comprising the compound of Formula 1 at a concentration above 5 wt. % based on total wt. of the product.

16. The solid material of claim 7, comprising the compound of Formula 1 at a concentration above 10 wt. % based on total wt. of the product.

17. The coating as claimed in claim 1, wherein when $X_1$ and $X_2$=NH,
 if R is phosphite substituted with Et,
  R' is not phenylene; 2-methyl-1,3-phenylene; 2,4,6-trimethyl-phenylene; 1,3-xylylene; diphenylmethane-4,4'-diyl; 1,2-ethylene; 1,3-propylene; 1,6-hexylene; 1,8-(3,6-dioxa octylene) or pyrid-2,6-diyl;
 if R is phosphite substituted with Me,
  R' is not 1,3-phenylene or dimethyl-1,3-propylene, and
 if R is phosphite substituted with iPr,
  R' is not 1,3-phenylene or 1,12-dodecylene.

18. The solid material as claimed in claim 7, wherein when $X_1$ and $X_2$=NH,
 if R is phosphite substituted with Et,
  R' is not phenylene; 2-methyl-1,3-phenylene; 2,4,6-trimethyl-phenylene; 1,3-xylylene; diphenylmethane-4,4'-diyl; 1,2-ethylene; 1,3-propylene; 1,6-hexylene; 1,8-(3,6-dioxa octylene) or pyrid-2,6-diyl;
 if R is phosphite substituted with Me,
  R' is not 1,3-phenylene or dimethyl-1,3-propylene, and
 if R is phosphite substituted with iPr,
  R' is not 1,3-phenylene or 1,12-dodecylene.

19. A method of making a flame-retardant coating material, the method comprising:
 incorporating a compound according to Formula 1 in a coating composition,

FORMULA 1

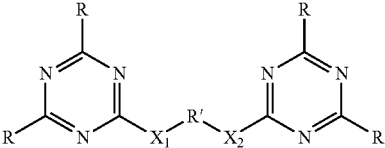

with R=phosphite substituted with alkyl, functionalized alkyl, aryl, functionalized aryl, except halogen-substituted alkyl or aryl;
R'=alkylene, arylene, alkoxy or aryloxy, all unsubstituted or functionalized, except halogen-substituted;
$X_1$ and $X_2$=hetero atoms and $X_1$ and $X_2$ are the same or different.

20. The method of claim 19, wherein the method comprises incorporating the compound according to Formula 1 in a lacquer.

21. The method of claim 19, wherein the method comprises incorporating the compound according to Formula 1 in a paint.

22. The method of claim 19, wherein when $X_1$ and $X_2$=NH,
 if R is phosphite substituted with Et,
  R' is not phenylene; 2-methyl-1,3-phenylene; 2,4,6-trimethyl-phenylene; 1,3-xylylene; diphenylmethane-4,4'-diyl; 1,2-ethylene; 1,3-propylene; 1,6-hexylene; 1,8-(3,6-dioxa octylene) or pyrid-2,6-diyl;
 if R is phosphite substituted with Me,
  R' is not 1,3-phenylene or dimethyl-1,3-propylene, and
 if R is phosphite substituted with iPr,
  R' is not 1,3-phenylene or 1,12-dodecylene.

23. A method of making a flame-retardant solid material, the method comprising:
 incorporating a compound according to Formula 1 in a solid composition,

FORMULA 1

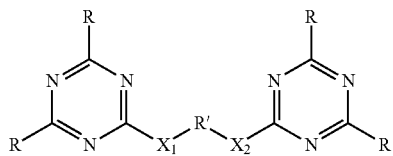

with R=phosphite substituted with alkyl, functionalized alkyl, aryl, functionalized aryl, except halogen-substituted alkyl or aryl;
R'=alkylene, arylene, alkoxy or aryloxy, all unsubstituted or functionalized, except halogen-substituted;
$X_1$ and $X_2$=hetero atoms and $X_1$ and $X_2$ are the same or different.

24. The method of claim 23, wherein the method comprises incorporating the compound according to Formula 1 in a wood-based material.

25. The method of claim 23, wherein the method comprises incorporating the compound according to Formula 1 in a plastic material.

26. The method of claim 23, wherein when $X_1$ and $X_2$=NH,
  if R is phosphite substituted with Et,
    R' is not phenylene; 2-methyl-1,3-phenylene;
    2,4,6-trimethyl-phenylene;
    1,3-xylylene; diphenylmethane-4,4'-diyl;
    1,2-ethylene; 1,3-propylene; 1,6-hexylene;
    1,8-(3,6-dioxa octylene) or pyrid-2,6-diyl;
  if R is phosphite substituted with Me,
    R' is not 1,3-phenylene or dimethyl-1,3-propylene, and
  if R is phosphite substituted with iPr,
    R' is not 1,3-phenylene or 1,12-dodecylene.

* * * * *

UNITED STATES PATENT AND TRADEMARK OFFICE
CERTIFICATE OF CORRECTION

PATENT NO. : 10,968,204 B2
APPLICATION NO. : 16/339787
DATED : April 6, 2021
INVENTOR(S) : Khalifah Salmeia, Sabyasachi Gaan and Markus Brühwiler Page 1 of 2

It is certified that error appears in the above-identified patent and that said Letters Patent is hereby corrected as shown below:

In the Claims

In Claim 2 (Column 8, Lines 5-9 (approx.)), 3rd Image 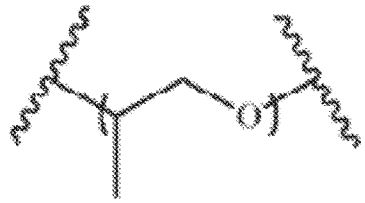 is replaced with 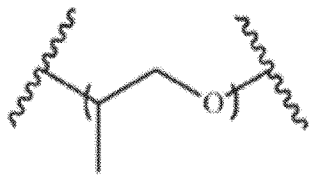 ;

In Claim 8 (Column 10, Lines 15-19 (approx.)), 3rd Image 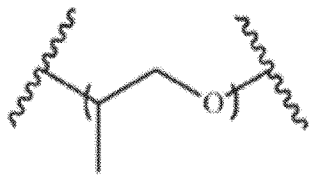 is replaced with Signed and Sealed this
Sixth Day of July, 2021

Drew Hirshfeld
*Performing the Functions and Duties of the
Under Secretary of Commerce for Intellectual Property and
Director of the United States Patent and Trademark Office*

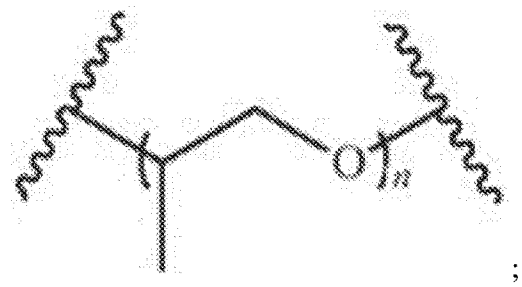
In Claim 19 (Column 12, Line 44), X₂₌hetero is replaced with X₂=hetero.